(12) United States Patent
Gleich

(10) Patent No.: US 8,903,482 B2
(45) Date of Patent: Dec. 2, 2014

(54) APPARATUS AND METHOD FOR NON-INVASIVE INTRACARDIAC ELECTROCARDIOGRAPHY USING MPI

(75) Inventor: Bernhard Gleich, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 444 days.

(21) Appl. No.: 13/392,626

(22) PCT Filed: Sep. 3, 2010

(86) PCT No.: PCT/IB2010/053970
§ 371 (c)(1),
(2), (4) Date: Feb. 27, 2012

(87) PCT Pub. No.: WO2011/030266
PCT Pub. Date: Mar. 17, 2011

(65) Prior Publication Data
US 2012/0172738 A1    Jul. 5, 2012

(30) Foreign Application Priority Data

Sep. 14, 2009 (EP) ..................................... 09170208

(51) Int. Cl.
*A61B 5/04* (2006.01)
*A61B 5/0402* (2006.01)
*A61B 5/05* (2006.01)

(52) U.S. Cl.
CPC ............. *A61B 5/0402* (2013.01); *A61B 5/0515* (2013.01)

USPC .......................................... 600/523; 600/509

(58) Field of Classification Search
CPC ... A61B 5/0006; A61B 5/0432; A61B 5/0402
See application file for complete search history.

(56) References Cited

FOREIGN PATENT DOCUMENTS

| WO | 2004091386 | 10/2004 |
|---|---|---|
| WO | 2004091390 | 10/2004 |
| WO | 2004091394 | 10/2004 |
| WO | 2004091395 | 10/2004 |
| WO | 2004091396 | 10/2004 |
| WO | 2004091397 | 10/2004 |
| WO | 2004091398 | 10/2004 |
| WO | 2004091408 | 10/2004 |

OTHER PUBLICATIONS

B. Gleich, et al., "Tomographic Imaging using the Nonlinear Response of Magnetic Particles", Nature, vol. 435, Jun. 30, 2005; doi: 10/1038, pp. 1214-1217.

*Primary Examiner* — Christopher D Koharski
*Assistant Examiner* — Philip Edwards

(57) ABSTRACT

The present invention relates to an apparatus and a corresponding method for non-invasive intracardiac electrocardiography (ECG) by use of a magnetic and electrically conducting interference device (210). An MPI-based ECG mapping technique is proposed, wherein an interference device (210), e.g. an electrically conducting rod containing soft magnetic material, is steered through the vessel system and the heart using magnetic fields generated by a magnetic particle imaging (MPI) system so that the ECG signals measured in parallel are influenced. Using appropriately adapted evaluation means (153) this influence of the interference device (210) on the ECG signals can be evaluated to gain spatially resolved information about the electrical heart activity.

11 Claims, 9 Drawing Sheets

APPARATUS AND METHOD FOR NON-INVASIVE INTRACARDIAC ELECTROCARDIOGRAPHY USING MPI

FIELD OF THE INVENTION

The present invention relates to an apparatus and a method for non-invasive intracardiac Electrocardiography (ECG) by use of a magnetic and electrically conducting interference device. Further, the present invention relates to a computer program for implementing said method on a computer and for controlling such an apparatus.

BACKGROUND OF THE INVENTION

Electrocardiography (ECG) is a widespread commonly used and well known technique for the recording of the electrical activity of the heart over time. ECG measurements can therefore reliably support the diagnosis of heart failures, like congestive heart failure, abnormal heart rhythms for example caused by dyssynchrony of cardiac contraction, arterial fibrillation or arterial flutter. An ECG device records the electric impulses of the heart, which originate in the sinoarterial node and travel through the intrinsic conducting system to the heart muscle, are recorded over time. In conventional ECGs the electrical depolarization wavefront is usually measured via electrodes which are placed at selective locations on the skin of the patient. The ECG device then displays the voltage between pairs of these electrodes flooded over time. The standard ECG therefore describes the time dependent characteristics of the electrical activity of the heart. Depending on the application the ECG measurement data can also be used in a so called vector ECG to describe the spatial characteristics of the electrical heart activities. In other words, within a vector ECG the ECG measurement data are used for imaging the spatial propagation of the depolarization wavefront over time. The depolarization wavefront is thereby often imagined as a three-dimensional vector (usually denominated as mean electrical vector) which has at every point in time a defined direction (the direction of propagation) and a defined length (depending on the voltage drop at the wavefront).

For many applications where more precise diagnoses are needed standard ECG devices are not accurate enough. In these situations intracardiac ECGs are performed. An intracardiac ECG (also denoted as ECG mapping) measures the electric potentials within specific cardiac regions by placing electrodes within the heart via a cardiac catheter. This technique is especially applied when the electrical activity of the heart needs to be evaluated in regions within the cardiac conducting system, such as for example in the region around the bundle of HiS, where no ECG signals can be acquired using a standard ECG device with body surface electrodes. The accuracy of an intracardiac mapping is therefore far beyond standard ECGs. ECG mapping is thus a very important technique for the planning of a catheter ablation procedure, which is used to remove a faulty electrical pathway from the heart.

The main disadvantage of an intracardiac ECG is its necessary invasive procedure where a catheter is introduced into the patient's blood vessels which are advanced towards the heart, usually either through the femoral vein, the internal jugular vein or through the subclavian vein. This represents a serious surgical intervention which is not only complex and time consuming but also uncomfortable and not without risk for the patient.

A non-invasive measurement technique having a comparably high accuracy as the intracardiac ECG is unfortunately not known so far.

Magnetic Particle Imaging (MPI) is an emerging medical imaging modality. The first versions of MPI were two-dimensional in that they produced two-dimensional images. Future versions will be three-dimensional (3D). A time-dependent, or 4D, image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, an MP image of an object's volume of interest is generated in two steps. The first step, referred to as data acquisition, is performed using an MPI scanner. The MPI scanner has means to generate a static magnetic gradient field, called "selection field", which has a single field free point (FFP) at the isocenter of the scanner. In addition, the scanner has means to generate a time-dependent, spatially nearly homogeneous magnetic field. Actually, this field is obtained by superposing a rapidly changing field with a small amplitude, called "drive field", and a slowly varying field with a large amplitude, called "focus field". By adding the time-dependent drive and focus fields to the static selection field, the FFP may be moved along a predetermined FFP trajectory throughout a volume of scanning surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning The object must contain magnetic nanoparticles; if the object is an animal or a patient, a contrast agent containing such particles is administered to the animal or patient prior to the scan. During the data acquisition, the MPI scanner steers the FFP along a deliberately chosen trajectory that traces out the volume of scanning, or at least the field of view. The magnetic nanoparticles within the object experience a changing magnetic field and respond by changing their magnetization. The changing magnetization of the nanoparticles induces a time dependent voltage in each of the receive coils. This voltage is sampled in a receiver associated with the receive coil. The samples output by the receivers are recorded and constitute the acquired data. The parameters that control the details of the data acquisition make up the scan protocol.

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model is an integral operator that acts on the acquired data; the reconstruction algorithm tries to undo, to the extent possible, the action of the model.

Such an MPI apparatus and method have the advantage that they can be used to examine arbitrary examination objects—e.g. human bodies—in a non-destructive manner and without causing any damage and with a high spatial resolution, both close to the surface and remote from the surface of the examination object. Such an arrangement and method are generally known and are first described in DE 101 51 778 A1 and in Gleich, B. and Weizenecker, J. (2005), "Tomographic imaging using the nonlinear response of magnetic particles" in nature, vol. 435, pp. 1214-1217. The arrangement and method for magnetic particle imaging (MPI) described in that publication take advantage of the non-linear magnetization curve of small magnetic particles.

SUMMARY OF THE INVENTION

It is an object of the present invention to provide an apparatus and a method for a non-invasive intracardiac electrocardiography (ECG), which supply a comparably high accuracy as the known intracardiac ECG mapping technique, are easier and faster to apply, do not require a surgical intervention and a therefore more comfortable for the patient.

In a first aspect of the present invention an apparatus is presented which comprises:

ECG means for recording ECG signals, selection means comprising a selection field signal generator unit and selection field elements, in particular selection field magnets or coils, for generating a magnetic selection field having a pattern in space of its magnetic field strength such that a first sub-zone having a low magnetic field strength and a second sub-zone having a higher magnetic field strength are formed in a field of view, drive means comprising a drive field signal generator unit and drive field coils for changing the position in space of the two sub-zones in the field of view by means of a magnetic drive field so that the magnetization of the interference device in the field of view changes locally, receiving means comprising at least one signal receiving unit and at least one receiving coil for acquiring detection signals, which detection signals depend on the magnetization of the interference device in the field of view, which magnetization is influenced by the change in the position in space of the first and second sub-zone, control means for controlling said signal generator units to generate and provide control currents to the respective field coils to generate appropriate magnetic fields for moving the interference device through the vessel system and the heart in a direction instructed by movement commands and/or for holding the interference device at a constant position, processing means for processing said detection signals acquired when appropriate magnetic fields are applied for determining the position of the interference device within the vessel system and the heart from the processed detection signals, and evaluation means for evaluating the influence of the interference device on the ECG signals recorded by the ECG means.

In a further aspect of the present invention a corresponding method is presented.

In still a further aspect of the present invention a computer program is presented comprising program code means for causing a computer to control the apparatus according to the present invention to carry out the steps of the method according to the present invention when said computer program is carried out on the computer.

Preferred embodiments of the invention are defined in the dependent claims. It shall be understood that the claimed method and the claimed computer program have similar and/or identical preferred embodiments as the claimed apparatus and as defined in the dependent claims.

It has been recognized by the inventors that the major limitation of the known intracardiac ECG mapping, the complex, time-consuming and invasive surgery using a catheter, can be overcome by making use of the MPI technology. Hence, the inventors of the present invention have found a solution to use a standard non-invasive ECG device by additionally using a magnetic and electrically conducting interference device, which is introduced into the examined object prior to the examination, which is then, during the examination, actively moved, tracked and imaged using a specially adapted MPI apparatus wherein the interference device exerts an influence on the ECG signals which can be evaluated. By steering and localizing the interference device in the heart of the patient using appropriate magnetic fields of the MPI apparatus according to the present invention, the interference device alters the electrical fields of the heart and therefore allows the reconstruction of spatially localized ECG signals. In other words, the inventors have found an MPI based ECG mapping technique, wherein an interference device, which can be imagined as an electrically conducting rod containing soft magnetic material, is steered through the vessel system and the heart using the focus and selection field of an MPI system so that the ECG signals are influenced. Using the adapted evaluation means of the apparatus according to the present invention, this influence of the interference device on the ECG signal can be evaluated in order to gain spatially resolved information about the electrical heart activity.

The major advantage of the apparatus according to the present invention is that the accuracy is, compared to standard ECGs, significantly increased. By use of the magnetic interference device the ECG required by the present invention is intracardiac, but nevertheless no invasive intervention is needed. The precision and the signal qualities are thereby comparable to known invasive intracardiac ECG mapping techniques even though no surgical intervention using a catheter is needed. Furthermore, the presented method is less time-consuming, more comfortable and less risky for the patient.

Preferably, the interference device is a very small magnetically and electrically conducting rod which is moved using the selection and the drive means of the apparatus according to the present invention. Thus, the interference device can be moved to any region within the blood vessels or the heart of the patient and thereby supply information about the tissue and the condition of the heart. Remembering that in known techniques a catheter has to be used, the presented method is much more flexible and allows to acquire ECG signals even for regions into which a catheter cannot be introduced.

The presented apparatus and method can, for example, be applied in the planning of a catheter ablation procedure. This would bring the advantage that the planning and the intervention of the catheter ablation procedure could be, in contrast to known methods, decoupled. According to methods known in the art, these two steps cannot be decoupled so that the intracardiac ECG map is always performed at the same time of the catheter ablation itself. This has the disadvantage that often the reasons for the arrhythmia cannot all be found during the ablation procedure so that several surgeries might be necessary. In contrast thereto, using the apparatus according to the present invention a longer, harmless and comfortable planning phase, which is decoupled from the actual intervention, can be distributed over several days so that the reasons for the arrhythmia can be reliably diagnosed.

The magnetic and electrically conducting interference device can be, as already mentioned above, imagined as a small rod containing soft magnetic material, which could be for example a small wire made of pure iron. Concerning the size of the interference device a length of 3 mm and a diameter of 200 μm are used in an implementation. It should be noted that the diameter of the device should not exceed 200 μm in order not to block relevant vessels. The length is preferably in the region of 1 mm to 10 mm. Even though longer devices would produce more signals, they may impose too high risk for harming the tissue, respectively the vessel. It has to be noted that the device could even be larger than the above-specified sizes if it is applied in different examination objects than the human heart. Furthermore, it is desirable if the interference device made of pure iron which degrades in the human body within a short time so that the interference device is dissolved in the blood.

According to a preferred embodiment of the invention the interference device is made of a biologically degradable polymeric material, such as polylactic acid, in which small magnetic and electrically conductive particles are integrated. This further decreases the risk for harming the tissue, respectively the vessel, since the above mentioned material degrades in the human body very quickly (within a few minutes).

Further advantages of the apparatus according to the present invention derive from the MPI technology. Since control means are provided to generate appropriate magnetic fields (the selection field and the drive field) for moving the interference device through the vessel system and the heart in a direction instructed by movement commands and/or for holding the interference device at a constant position, the interference device can be moved to any place within the heart only by applying magnetic forces so that the planning procedure is thereby enormously facilitated and the accuracy of the placement of the interference device is significantly increased compared to the known catheter intervention. The control means are thereby adapted to modify the magnetic fields very fast so that the movement and placement of the interference device can be conducted in a very short time. As already mentioned above, the measurement can be, due to its non-invasive character, repeated many times without providing a risk for the patient.

The movement of the interference device is thereby preferably instructed by movement commands which can be defined in a planning step. Preferably, an interface for inputting such movement commands to the control unit is provided. Such an interface can be a user interface, such as a keyboard, pointer, computer mouse or joystick, or an interface for connection to another apparatus, such as a navigation unit or navigation tool on a computer, on which, for instance, the movement of the interference device has been planned, e.g. by use of image data of the patient obtained by use of another imaging modality, such as MR or CT.

Due to the provided processing means the interference device can be localized and visualized at any time during the ECG measurement. Compared to the known intracardiac ECG mapping, no additional hardware, such as a camera system or an X-ray system, is needed for the visualization and/or the localization of the interference device since the device can be moved and localized alternately or even almost simultaneously without additional equipment. Since no X-ray is needed compared to known methods where the catheter has to be imaged using X-ray, the dosage for the patient is also reduced.

According to a preferred embodiment of the present invention, the above-mentioned ECG signals are recorded by the ECG means by use of skin electrodes which are arranged on the skin of the patient. This means that the ECG signals can be recorded by regular ECG means using body surface electrodes. Nevertheless, the precision and the signal quality are, as explained above, far beyond that of a regular ECG device.

Furthermore, production costs of the apparatus according to the present invention can be saved if regular ECG devices can be used and only need to be adapted according to the present invention. To improve the signal quality and the measurement accuracy, the application of multiple ECG skin electrodes is desirable.

According to a further preferred embodiment of the present invention, the ECG signals are measured for a plurality of positions of the interference device. This means that the interference device is actively positioned on a plurality of positions within the heart so that during the measurement the influence of the interference device on the ECG signals can be recorded by the evaluation means for all regions within the heart. Thereby a spatially resolved "map" can be established which shows the influence of the interference device on the ECG signals. Thus, it is possible to locate regions where possible arrhythmia results from or scarred tissue occurs.

According to a further preferred embodiment the evaluation means are adapted for evaluating signal modulations of the ECG signals resulting from changes of the electrical field caused by the interference device. If the interference device is placed within the heart, the electrical conductivity is changed at this position due to the electrically conducting characteristics of the device so that the ECG signal is modulated when the depolarization wavefront of the heart passes the position of the interference device. The interference device thereby alters the field lines of the electrical field of the depolarization wavefront and therefore modulates the ECG signal. The interference device is, during the measurement, either kept at a defined position (using the magnetic fields) until the depolarization wavefront has passed the interference device at least once or it is released and therefore moved with the blood flow on a random path while the position and orientation is precisely tracked using the processing means. In this case the speed of the device may exceed 1 m/s so that the ECG signal now is modulated at frequencies above 300 Hz. Therefore, the modulation frequencies are in another frequency band than the ECG signals so that the "signature" of the interference device can be easily extracted in the Fourier space.

One of the advantages of the occurrence of these signal modulations on the ECG signal is that for example scarred tissue can be determined since no or a rather weak modulation occurs if the interference device is located at a position where the tissue is scarred. This results from the fact that scarred tissue has a significantly decreased electrical conductivity so that the depolarization wavefront could be imagined as moving around the scarred tissue (the propagation wavefront "avoids" the depolarization wavefront).

In order to evaluate the signal modulations resulting from the changes of the electric field caused by the interference device, it is according to an embodiment of the present invention furthermore preferred that the evaluation means are adapted for bringing the information about the signal modulations of the ECG signals caused by the interference device into correlation over time with the information about the position of the interference device within the vessel and the heart determined from the processed detection signals. The major improvement of this measure is that according to this embodiment the spatial information about the location of the interference device, which is acquired using the MPI tracking technique, is brought into correlation with the time-dependent signal modulation of the ECG signals. This means that when a specific ECG feature is most modulated when the device is at a certain position, the ECG feature originates from the position which is acquired by the MPI tracking technique.

If for example the interference device is located near the sinoarterial node the P wave of the ECG signal will be most modulated whereas the strength of the modulation decreases further away from the P wave. Bringing the spatial and time-dependent information together in this example means that the time the depolarization wavefront needs to propagate from the sinoarterial node to the specific position, where the interference device is located, can be taken from the ECG signal by measuring the time from the start of the ECG signal to the point of the strongest modulation, on the other hand, the position of the interference device can be accurately determined using a processing means of the MPI apparatus. In this way the exact time- and spatially dependent propagation of the depolarization wavefront can be determined.

According to a further embodiment of the present invention, it is proposed that the evaluation means are adapted for determining the mean electrical vector of the polarization wavefront of the heart over time at a spatially determined position by bringing the information about the signal modulations of the ECG signals caused by the interference device into correlation over time with the information about the position of the interference device within the vessel system and the heart determined from the process detection signals. Similar to a conventional vector ECG, where the ECG data are used for imaging the spatial propagation of the depolarization wavefront over time, the mean electrical vector, which denotes the propagation direction and the voltage drop at the wavefront at every point in time, can be very accurately determined for every position in the heart. In contrast to known non-invasive (regular) ECGs, where this mean electrical vector is reconstructed only based on approximate simulation modules, the mean electrical vector can be determined according to the present invention based on concrete measured signals and based on concrete mathematical calculations. This possibility is so far only known from the invasive catheter ECG mapping, which has the disadvantage that a serious surgical intervention is necessary. If the mean electrical vector of the depolarization wavefront is determined for sufficient positions within the heart, a very accurate propagation of the depolarization wavefront can be reconstructed over time.

According to a further embodiment of the present invention, the apparatus according to the present invention additionally comprises quality improvement means for improving the evaluation of said signal modulations by comparing the measured signal modulations with expected signal modulations. The quality of the reconstruction of the depolarization wavefront is thus significantly improved. In practice, this is for example done by adapting the measured values for the mean electrical vector with expected modulated values, for example using an interpolation.

According to a further preferred embodiment of the present invention, the apparatus comprises imaging means for imaging the propagation of the depolarization wavefront over time. Thereby, the simulation of the propagation of the depolarization wavefront can be imaged for example on a screen of a computer so that anomalies or other heart failures can be realistically imaged. In this way the diagnosis of heart diseases can be significantly improved.

According to a still further preferred embodiment of the present invention, the apparatus furthermore comprises focus means comprising a focus field signal generator unit and focus field coils for changing the position in space of the field of view by means of a magnetic focus field. Such a focus field has the same or a similar spatial distribution as the drive field. The focus field is basically used to move the position in space of the field of view. This is especially necessary since the field of view has a very limited size so that, if the target element needs to be moved over a longer distance within the examination object (the patient), the focus field needs to change the position in space of the field of view in order to actively move and track the interference device over its entire path until it has reached its desired position within the heart of the patient.

In other words, the focus field replaces the active mechanical movement of the patient. This means that the patient would need to be moved physically in order to move the field of view if no focus field means are provided. Same or even better as the magnetic drive field coils the magnetic focus field coils can be used for the movement of the interference device through the patient. These coils are able to generate sufficiently homogenous fields in various directions at a sufficiently high speed and with sufficiently large field strengths that are required for the movement of the interference device. The use of these focus field coils therefore provides a high flexibility since they can be generated in any direction.

As already mentioned above, the focus field has the same or a similar spatial distribution as the drive field. It is even possible to use the same magnetic coils as the coils are used to generate the magnetic drive field. The basic difference is that the frequencies are much lower (e.g. <1 kHz, typically <100 Hz) for the focus field than for the drive field, but the amplitudes of the focus field are much higher (e.g. 200 mT compared to 20 mT for the drive field).

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in detail with reference to FIGS. 1 to 3. In particular, two embodiments of an MPI scanner for medical diagnostics will be described. An informal description of the data acquisition is also given. The similarities and differences between the two embodiments will be pointed out.

Figure 1:
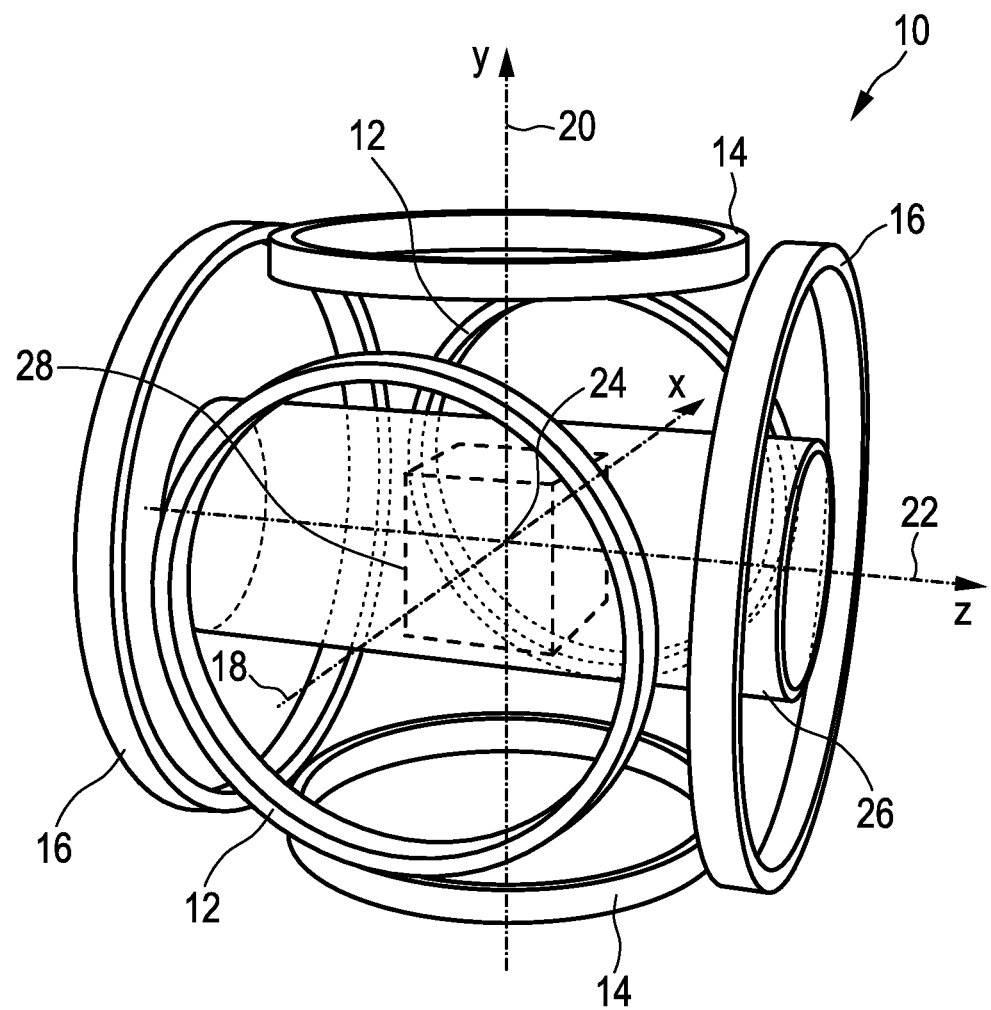
FIG. 1 shows a first embodiment of an MPI apparatus.

The first embodiment 10 of an MPI scanner shown in FIG. 1 has three prominent pairs 12, 14, 16 of coaxial parallel circular coils, each pair being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x and z-axes are horizontal. The coil pairs 12, 14, 16 are also named after their axes. For example, the y-coil pair 14 is formed by the coils at the top and the bottom of the scanner. Moreover, the coil with the positive (negative) y-coordinate is called the $y^+$-coil ($y^-$-coil), and similarly for the remaining coils.

The scanner 10 can be set to direct a predetermined, time dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the $z^+$-coil, and the current $-I^S$ is made to flow through the $z^-$-coil. The z-coil pair 16 then acts as an anti-parallel circular coil pair.

Figure 2:
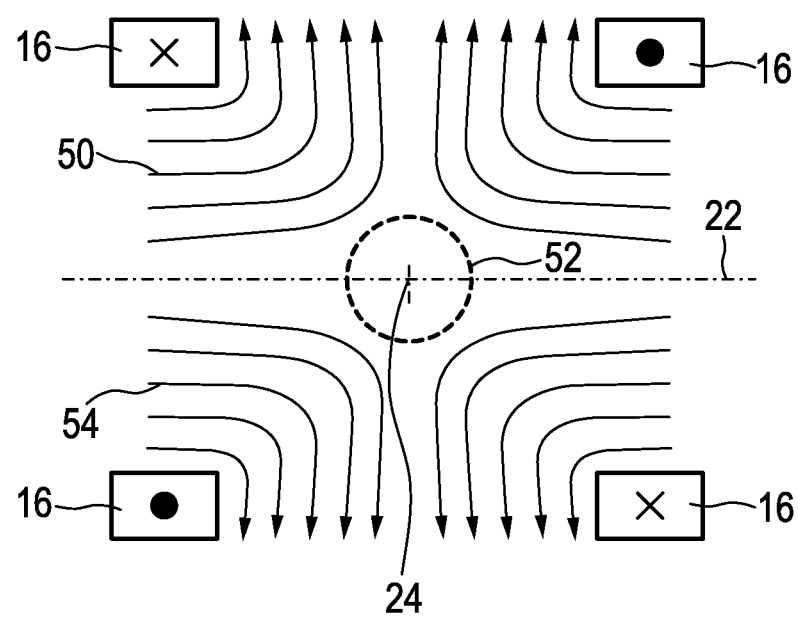
FIG. 2 shows an example of the selection field pattern produced by an apparatus as shown in FIG. 1.

The magnetic selection field which is generally a gradient magnetic field is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field 50 increases in all three spatial directions as the distance increases from the field-free point. In a first sub-zone or region 52 which is denoted by a dashed line around the isocenter 24 the field strength is so small that the magnetization of particles present in that first sub-zone 52 is not saturated, whereas the magnetization of particles present in a second sub-zone 54 (outside the region 52) is in a state of saturation. The field-free point or first sub-zone 52 of the scanner's field of view 28 is preferably a spatially coherent area; it may also be a punctiform area, a line or a flat area. In the second sub-zone 54 (i.e. in the residual part of the scanner's field of view 28 outside of the first sub-zone 52) the magnetic field strength of the selection field is sufficiently strong to keep the magnetic particles in a state of saturation.

By changing the position of the two sub-zones 52, 54 within the field of view 28, the (overall) magnetization in the field of view 28 changes. By measuring the magnetization in the field of view 28 or physical parameters influenced by the magnetization, information about the spatial distribution of the magnetic particles in the field of view 28 can be obtained. In order to change the relative spatial position of the two sub-zones 52, 54 in the field of view 28, further magnetic fields, i.e. the magnetic drive field, and, if applicable, the magnetic focus field, are superposed to the selection field 50 in the field of view 28 or at least in a part of the field of view 28.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field. The current flowing through the $z^\pm$-coil is $I^D_3 + I^F_3 \pm I^S$. The current flowing through the remaining two coil pairs 12, 14 is $I^D_k + I^F_k$, k=1, 2. Because of their geometry and symmetry, the three coil pairs 12, 14, 16 are well decoupled. This is wanted.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time dependent. The difference between the focus field and the drive field is that the focus field varies slowly in time and has a large amplitude while the drive field varies rapidly and has a small amplitude. There are physical and biomedical reasons to treat these fields differently. A rapidly varying field with a large amplitude would be difficult to generate and hazardous to the patient.

The embodiment 10 of the MPI scanner has at least one further pair, preferably three further pairs, of parallel circular coils, again oriented along the x-, y-, and z-axes. These coil pairs, which are not shown in FIG. 1, serve as receive coils. As with the coil pairs 12, 14, 16 for the drive and focus fields, the magnetic field generated by a constant current flowing through one of these receive coil pairs is spatially nearly homogeneous within the field of view and parallel to the axis of the respective coil pair. The receive coils are supposed to be well decoupled. The time dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from DC up to the point where the expected signal level drops below the noise level.

The embodiment 10 of the MPI scanner shown in FIG. 1 has a cylindrical bore 26 along the z-axis 22, i.e. along the axis of the selection field. All coils are placed outside this bore 26. For the data acquisition, the patient (or object) to be imaged (or treated) is placed in the bore 26 such that the patient's volume of interest—that volume of the patient (or object) that shall be imaged (or treated)—is enclosed by the scanner's field of view 28—that volume of the scanner whose contents the scanner can image. The patient (or object) is, for instance, placed on a patient table. The field of view 28 is a geometrically simple, isocentric volume in the interior of the bore 26, such as a cube, a ball, or a cylinder. A cubical field of view 28 is illustrated in FIG. 1.

The size of the first sub-zone 52 is dependent on the one hand on the strength of the gradient of the magnetic selection field and on the other hand on the field strength of the magnetic field required for saturation. For a sufficient saturation of the magnetic particles at a magnetic field strength of 80 A/m and a gradient (in a given space direction) of the field strength of the magnetic selection field amounting to $50 \times 10^3$ A/m$^2$, the first sub-zone 52 in which the magnetization of the particles is not saturated has dimensions of about 1 mm (in the given space direction).

The patient's volume of interest is supposed to contain magnetic nanoparticles. Especially prior to a therapeutic and/or diagnostic treatment of, for example, a tumor, the magnetic particles are positioned in the volume of interest, e.g. by means of a liquid comprising the magnetic particles which is injected into the body of the patient (object) or otherwise administered, e.g. orally, to the patient.

An embodiment of magnetic particles comprises, for example, a spherical substrate, for example, of glass which is provided with a soft-magnetic layer which has a thickness of, for example, 5 nm and consists, for example, of an iron-nickel alloy (for example, Permalloy). This layer may be covered, for example, by means of a coating layer which protects the particle against chemically and/or physically aggressive environments, e.g. acids. The magnetic field strength of the magnetic selection field 50 required for the saturation of the magnetization of such particles is dependent on various parameters, e.g. the diameter of the particles, the used magnetic material for the magnetic layer and other parameters.

In the case of e.g. a diameter of 10 μm, a magnetic field of approximately 800 A/m (corresponding approximately to a flux density of 1 mT) is then required, whereas in the case of a diameter of 100 μm a magnetic field of 80 A/m suffices. Even smaller values are obtained when a coating of a material having a lower saturation magnetization is chosen or when the thickness of the layer is reduced. Magnetic particles that can generally be used are available on the market under the trade name Resovist.

For further details of the generally usable magnetic particles and particle compositions, the corresponding parts of EP 1304542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

The data acquisition starts at time $t_s$ and ends at time $t_e$. During the data acquisition, the x-, y-, and z-coil pairs 12, 14, 16 generate a position- and time dependent magnetic field, the applied field. This is achieved by directing suitable currents through the coils. In effect, the drive and focus fields push the selection field around such that the FFP moves along a preselected FFP trajectory that traces out the volume of scanning—a superset of the field of view. The applied field orientates the magnetic nanoparticles in the patient. As the applied field changes, the resulting magnetization changes too, though it responds nonlinearly to the applied field. The sum of the changing applied field and the changing magnetization induces a time dependent voltage $V_k$ across the terminals of receive coil pair along the $x_k$-axis. The associated receiver converts this voltage to a signal $S_k(t)$, which it samples and outputs.

It is advantageous to receive or to detect signals from the magnetic particles located in the first sub-zone 52 in another frequency band (shifted to higher frequencies) than the frequency band of the magnetic drive field variations. This is possible because frequency components of higher harmonics of the magnetic drive field frequency occur due to a change in magnetization of the magnetic particles in the scanner's field of view 28 as a result of the non-linearity of the magnetization characteristics.

Figure 3:
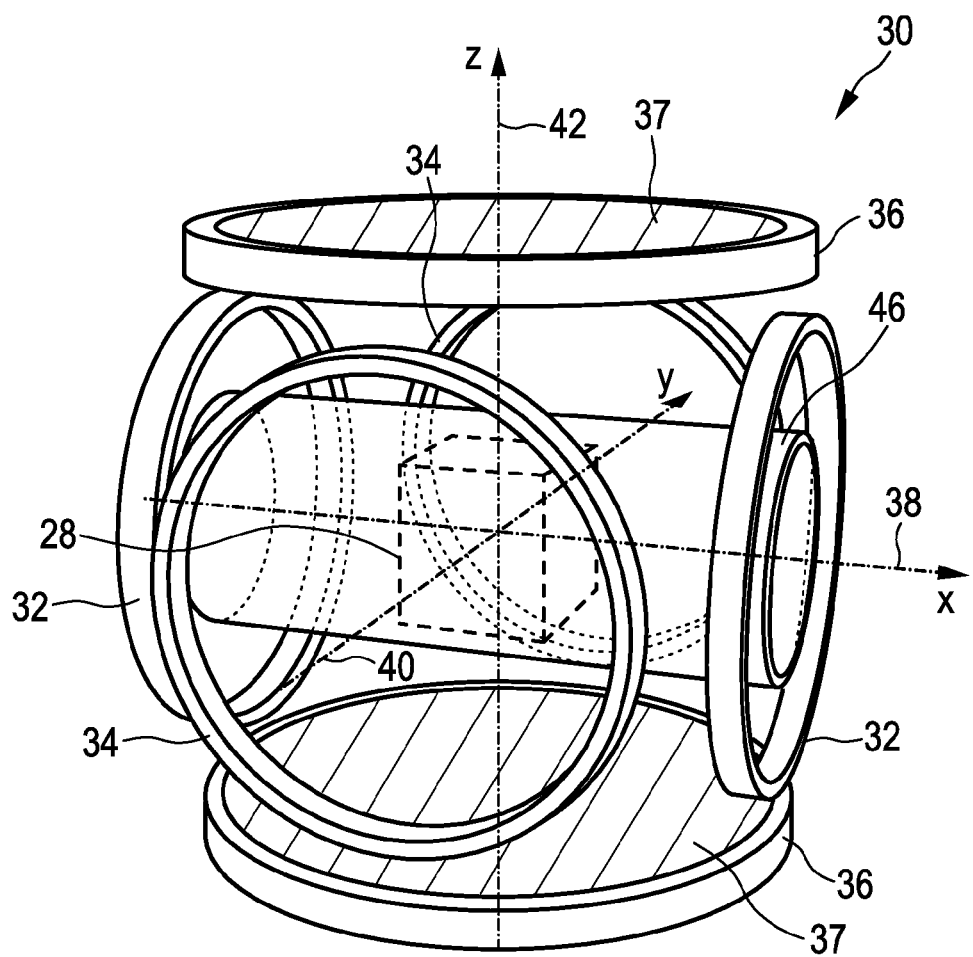
FIG. 3 shows a second embodiment of an MPI apparatus.

Like the first embodiment 10 shown in FIG. 1, the second embodiment 30 of the MPI scanner shown in FIG. 3 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The drive field is generated by a solenoid (not shown) along the x-axis 38 and by pairs of saddle coils (not shown) along the two remaining axes 40, 42. These coils are wound around a tube which forms the bore. The drive field coils also serve as receive coils. The signals picked up by the receive coils are sent through a high-pass filter that suppresses the contribution caused by the applied field.

To give a few typical parameters of such an embodiment: The z-gradient of the selection field, G, has a strength of $G/\mu_0=2.5$ T/m, where $\mu_0$ is the vacuum permeability. The selection field generated does either not vary at all over the time or the variation is comparably slow, preferably between approximately 1 Hz and approximately 100 Hz. The temporal frequency spectrum of the drive field is concentrated in a narrow band around 25 kHz (up to approximately 100 kHz). The useful frequency spectrum of the received signals lies between 50 kHz and 1 MHz (eventually up to approximately 10 MHz). The bore has a diameter of 120 mm. The biggest cube 28 that fits into the bore 46 has an edge length of 120 mm/√2≈84 mm.

As shown in the above embodiments the various magnetic fields can be generated by coils of the same coils pairs and by providing these coils with appropriately generated currents. However, and especially for the purpose of a signal interpretation with a higher signal to noise ratio, it may be advantageous when the temporally constant (or quasi constant) selection field and the temporally variable drive field and focus field are generated by separate coil pairs. Generally, coil pairs of the Helmholtz type can be used for these coils, which are generally known, e.g. from the field of magnetic resonance apparatus with open magnets (open MRI) in which a radio frequency (RF) coil pair is situated above and below the region of interest, said RF coil pair being capable of generating a temporally variable magnetic field. Therefore, the construction of such coils need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

Figure 4:
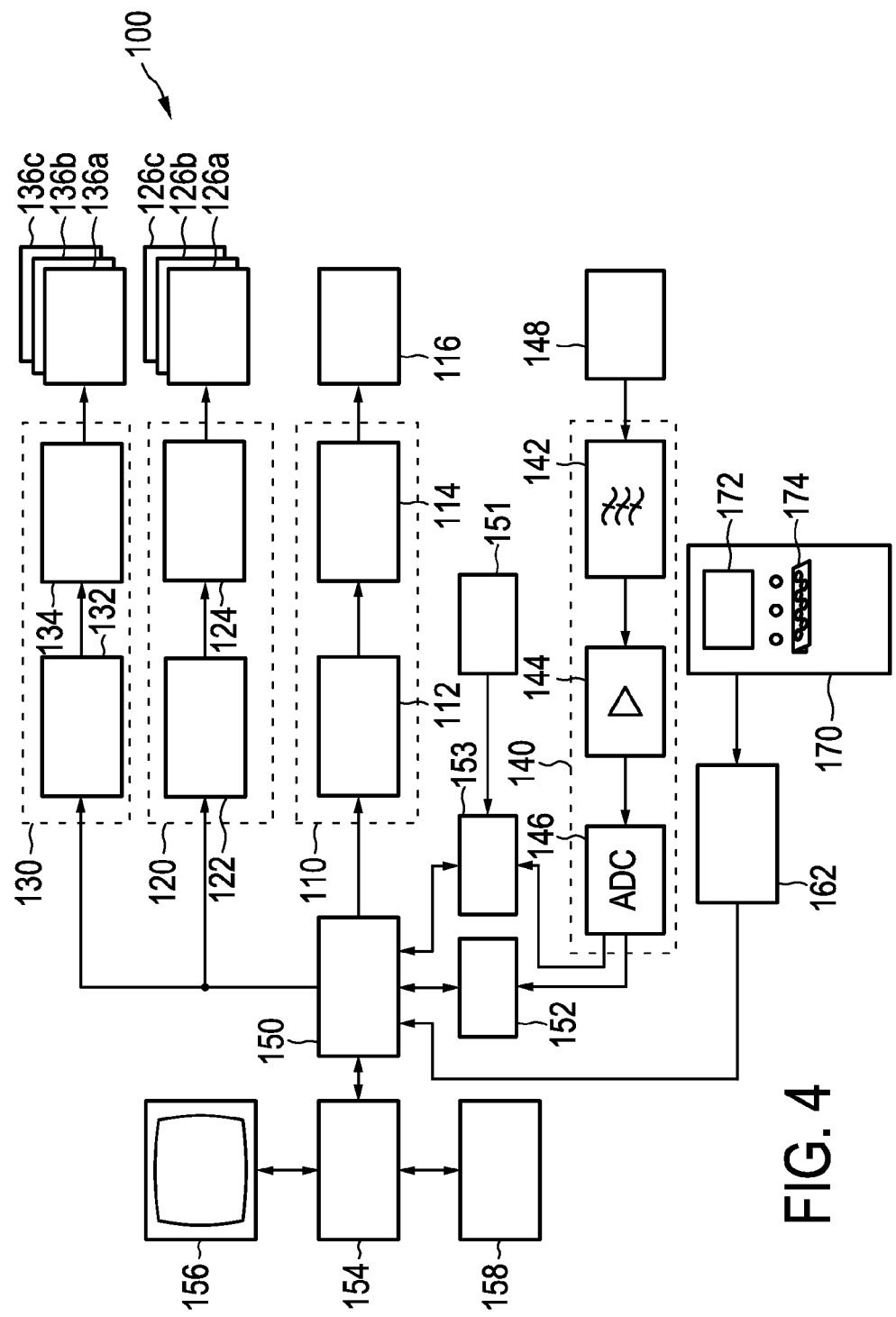
FIG. 4 shows a block diagram of an embodiment of the apparatus according to the present invention, FIG. 5 schematically shows the practical application of the apparatus according to the present invention.

FIG. 4 shows a block diagram of an apparatus 100 according to an embodiment of the present invention. The general principles of magnetic particle imaging explained above are valid and applicable to this embodiment as well, unless otherwise specified.

The embodiment of the apparatus 100 shown in FIG. 4 comprises a set of various coils for generating the desired magnetic fields. First, the coils and their functions in a MPI mode shall be explained.

For generating the magnetic gradient selection field explained above, selection means are provided comprising a set of selection field (SF) coils 116, preferably comprising at least one pair of coil elements. The selection means further comprises a selection field signal generator unit 110. Preferably, a separate generator subunit is provided for each coil (or each pair of coil elements) of the set 116 of the selection field coils. Said selection field signal generator unit 110 comprises a controllable selection field current source 112 (generally including an amplifier) and filter unit (114) which provide selective selection field coil elements with the selection field current to individually set the gradient strength of the selection field in the desired direction. Preferably, a DC current is provided. If the selection field coil elements are arranged as opposed coils, e.g. on opposite sides of the field of view, the selection field currents of opposed coils are preferably oppositely oriented.

The selection field signal generator unit 110 is controlled by a control unit 150, which preferably controls the selection field current generation 110 such that the sum of the field strength and the sum of the gradient strength of all spatial fractions of the selection field is maintained at a predefined level.

For the generation of a magnetic focus field the apparatus 100 further comprises focus means comprising a set of focus field (FF) coils, preferably comprising three pairs 126a, 126b, 126c of oppositely arranged focus field coil elements. Said magnetic focus field coils are controlled by a focus field signal generator unit 120, preferably comprising a separate focus field signal generator subunit for each coil element (or at least each pair of coil elements) of said sets of focus field coils. Said focus field signal generator unit 120 comprises a focus field current source 122 (preferably comprising a current amplifier) and a filter unit 124 for providing a focus field current to the respective coil of said subset of coils 126a, 126b, 126c which shall be used for generating the magnetic focus field. The focus field current unit 120 is also controlled by the control unit 150.

The focus field and its above-mentioned focus field generation means are according to the present invention not obligatory. The focus field means can be used, same as the drive field means (explained in detail below) can be used for moving the interference device 210 through the vessels of the patient 300 until it has reached its final desired position within the heart 220 of the patient 300. The interference device 210 is thereby moved via magnetic forces which occur due to the applied focus field (respectively due to the applied drive field). The focus field is furthermore preferred since the field of view 28 has a very limited size so that, if the interference device 210 needs to be moved over a longer distance through the vessels of the patient 300, the focus field needs to change the position in space of the field of view 28 in order to being able to actively move and track the interference device 210 over its entire path until it has reached its desired position within the heart 220 of the patient 300. In other words, the focus field replaces the active mechanical movement of the patient 300. If no focus field means are provided, the patient 300 would need to be moved physically in order to move the field of view 28.

For generation of the magnetic drive field, the apparatus 100 further comprises drive means comprising a subset of drive field (DF) coils, preferably comprising three pairs 136a, 136b, 136c of oppositely arranged drive field coil elements. The drive field coils are controlled by a drive field signal generator unit 130, preferably comprising a separate drive field signal generator subunit for each coil element (or at least each pair of coil elements) of said set of drive field coils. Said drive field signal generator unit 130 comprises a drive field current source 132 (preferably including a current amplifier) and a filter unit 134 for providing a drive field current to the respective drive field coil. The drive field current source 132 is adapted for generating an AC current and is also controlled by the control unit 150.

For signal detection receiving means 148, in particular a receiving coil, and a signal receiving unit 140, which receives signals detected by said receiving means 148, are provided. Said signal receiving unit 140 comprises a filter unit 142 for filtering the received detection signals. The aim of this filtering is to separate measured values, which are caused by the magnetization in the examination area which is influenced by the change in position of the two part-regions 52, 54, from other, interfering signals. To this end, the filter unit 142 may be designed for example such that signals which have temporal frequencies that are smaller than the temporal frequencies with which the receiving coil 148 is operated, or smaller than twice these temporal frequencies, do not pass the filter unit 142. The signals are then transmitted via an amplifier unit 144 to an analogue/digital converter 146 (ADC). The digitalized signals produced by the analogue/digital converter 146 are fed to an image processing unit (also called reconstruction means) 152, which reconstructs an image of the position of the interference device 210 so that the interference device 210 can be accurately and constantly tracked during the measurement. The reconstructed image of the position of the magnetic interference device 210 is finally transmitted via the control means 150 to a computer 154, which displays it on a monitor 156. Thus, an image can be displayed showing the position of the interference device 210.

Further, an input unit 158 is provided, for example a keyboard. A user is therefore able to set the desired direction of the highest resolution and in turn receives the respective image of the region of action on the monitor 156. If the critical direction, in which the highest resolution is needed, deviates from the direction set first by the user, the user can still vary the direction manually in order to produce a further image with an improved imaging resolution. This resolution improvement process can also be operated automatically by the control unit 150 and the computer 154.

According to the present invention, the control unit 150 is adapted for controlling the signal generator units 110, 120, 130, in particular the focus field signal generator unit 120 and/or the drive field signal generator unit 130, to generate and provide control currents to the respective field coils, in particular the focus field coils 126a, 126b, 126c and/or the drive field coils 136a, 136b, 136c to generate appropriate magnetic fields for moving the interference device 210 through the vessel system and the heart 220 in a direction instructed by movement commands and/or for holding the interference device 210 at a constant position. Thereby the interference device 210 can be moved to the desired position in the heart 220 of the patient 300. This movement can be executed very fast and is additionally much more comfortable and without any risk for the patient 300.

For inputting movement commands, an interface 162 is provided. Said interface 162 can be implemented in various ways. For instance, said interface 162 can be a user interface by which the user can manually input user commands, such as via a keyboard, a console, a joystick or a navigation tool, e.g. installed on a separate computer (not shown).

Hence, in effect, the apparatus according to the present invention is able to move the interference device 210 through the patient 300, in particular to control the direction of movement of the interference device 210, based on movement commands, irrespective in which form and by whom or what the movement commands have been provided.

The movement commands can also be received from an external movement control unit 170, which is connected to the interface 162, and which comprises a display 172, e.g. for displaying pre-acquired image data of the patient's heart 220, and an operator control 174 for inserting control commands for planning the movement of the interference device 210.

In a practical intervention the measurement can be planned in advance using the movement control unit 70. The navigation plan, in particular the movement control commands, are then provided via the interface 162 to the control unit 150 of the apparatus 100. At desired (e.g. regular) intervals the movement of the interference device 210 is stopped and its current position is acquired by applying an MPI sequence, preferably while moving the FFP along a trajectory through the area in which the interference device 210 might be currently located, and acquiring detection signals, which are then processed to get the current position of the interference device 210.

Thus, a direct feedback can be obtained whether or not the actual position of the interference device 210 corresponds to the desired position, so that immediate corrections can be made, either manually or by the control unit 150.

As explained above, an apparatus 100 is provided using the MPI imaging and tracking technique. According to the present invention, the apparatus 100 furthermore comprises ECG means 151 for recording ECG signals of the patient's heart 220. These ECG means 151 can be implemented by use of a standard ECG device which records the ECG signals by use of skin electrodes 230 (see FIG. 5). The ECG signals are then transferred to an evaluation means 153 which is adapted for evaluating the influence of the interference device 210 on the ECG signal. This evaluation means 153 can be for example another processing unit which is also connected to the control unit 150 and to the receiving means. In the evaluation means 153, the information about the heart activity of the patient and the influence of the interference device 210 on the ECG signal received by the ECG means 151 are brought together with the positioning information of the interference device 210 received by the receiving means.

In order to understand the principle of this evaluation which is performed by the evaluation means 153, examples will be given in the following and the principle will be further detailed.

Figure 5:
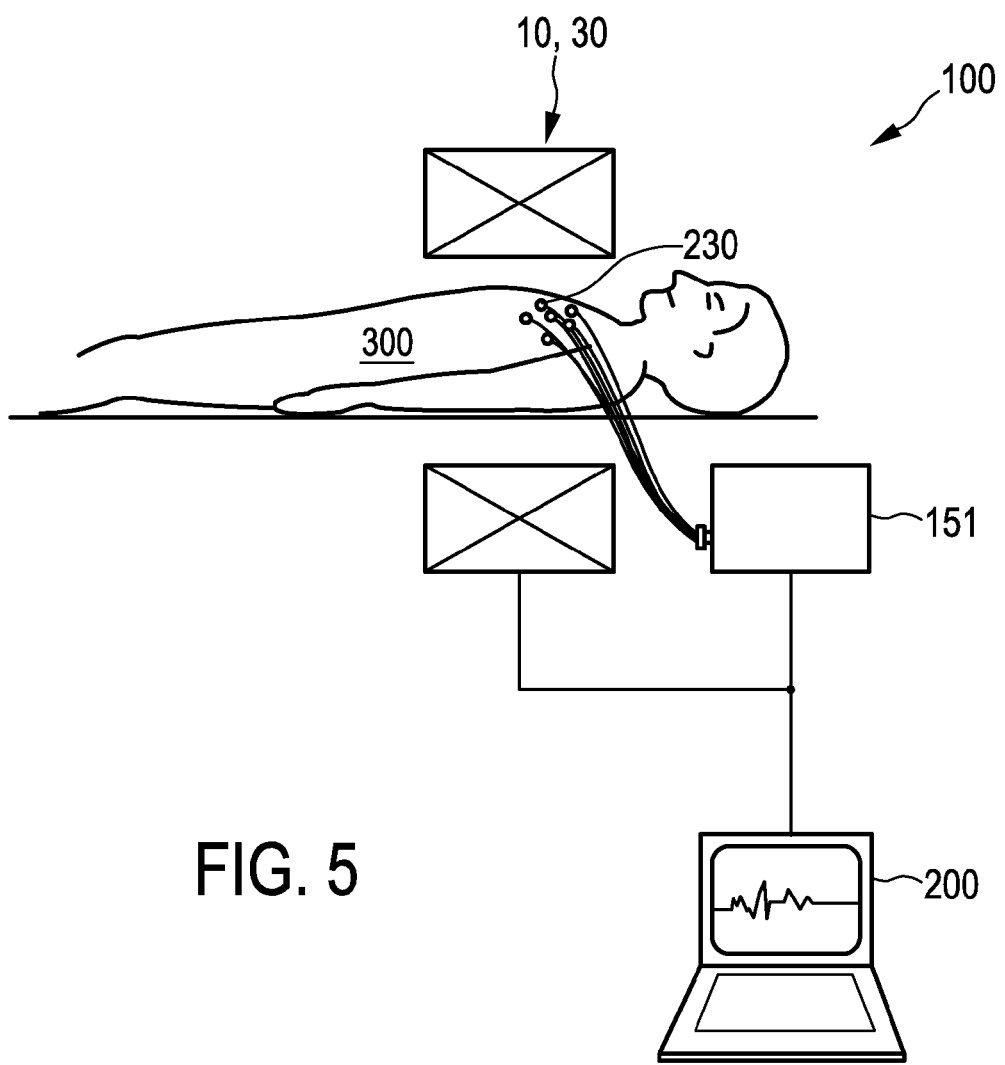

FIG. 5 schematically shows an embodiment of a practical measurement setup of the apparatus according to the present invention. The apparatus 100 thereby includes MPI means 10, 30 as the ones explained according to FIGS. 1 and 3, an ECG device 151 and a computer 200 which brings the information received from the MPI means 10, 30 and the ECG means 151 into correlation with each other and evaluates the measurement results. In detail, the interference device 210, which is preferably introduced into the patient 300 prior to the measurement, is moved (while, preferably, being constantly tracked) to the heart 220 of the patient using the above-mentioned MPI technique. The control unit 150, the imaging processing unit 152 and the evaluation means 153 are in this embodiment included in a computer 200 and not graphically shown again in detail. The apparatus 100 furthermore comprises an ECG device 151 which measures the ECG signals by using standard or slightly adapted skin electrodes 230. It has to be noted that suitable electrodes 230 are preferably non-magnetic, such as for example electrodes known in the field of MRI (Magnetic Resonance Imaging).

Figure 6A:
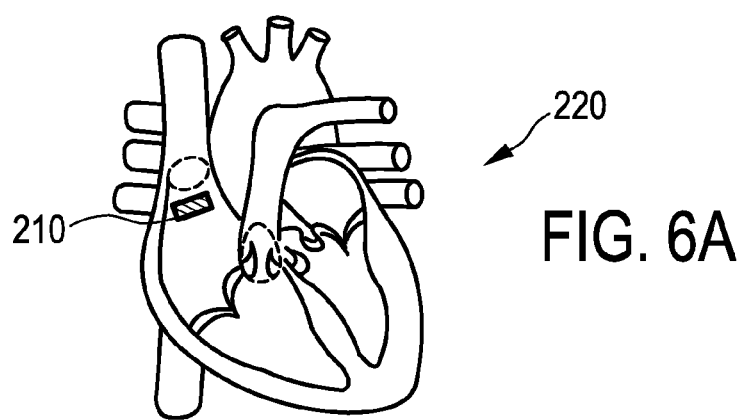
FIGS. 6A-6C show the positioning of an electrically conducting interference device according to the present invention at different positions in the heart.

If the interference device 210 is positioned in the heart 220 of the patient 300, it increases the electrical conductivity at this position due to its electrically conducting characteristics. As a result, the interference device 210 alters the electrical field of the heart activity when the depolarization wavefront of the heart 220 passes the interference device 210. This influence then results in a modulation of the ECG signal which is acquired by the ECG device 151. The modulation can be even increased if the interference device 210 is forced to rotate (using the magnetic fields of the MPI apparatus) while keeping it at a fixed position in the heart. This modulation 240 is exemplarily shown in FIG. 7A which shows a modulation 240 of the P wave of an exemplary ECG signal. The modulation frequency which is induced by the interference device 210 is even higher (above 300 Hz) than exemplarily shown in FIG. 7A. It also has to be noted that the amplitudes of the modulation are in reality usually smaller than the ones shown in FIG. 7, which are only exaggerated for illustration reasons. The measurement signal shown in FIG. 7A could correspond to a position of the interference device 210 which is exemplarily shown in FIG. 6A. In FIG. 6A, the interference device 210 is placed near the sinoarterial node.

Since the P wave of the ECG signal corresponds to the depolarization near the sinoarterial node, it is understandable that in case the interference device 210 is positioned in this region, also the P wave gets modulated as shown in FIG. 7.

Figure 6B:
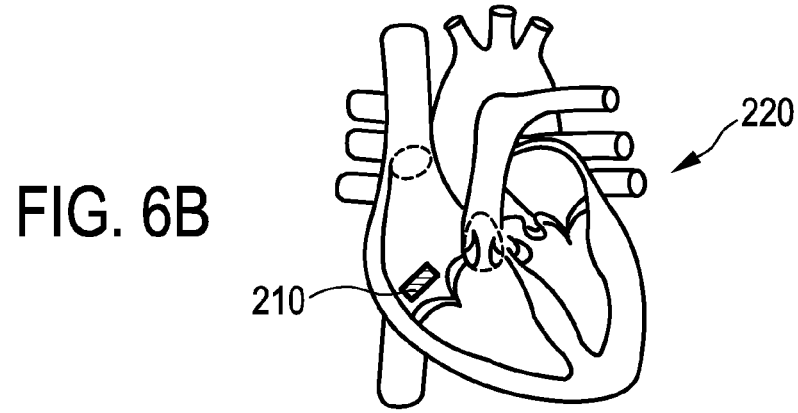
Figure 6C:
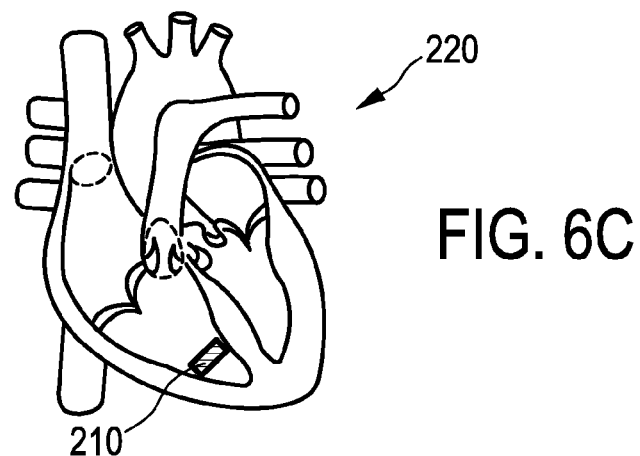
Figure 7A:
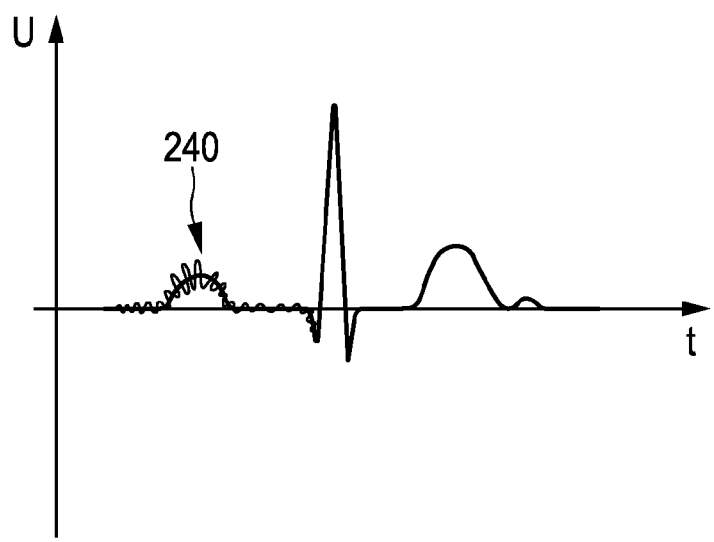
FIG. 7 shows the influence of the interference device according to the present invention on an ECG signal.
Figure 7B:
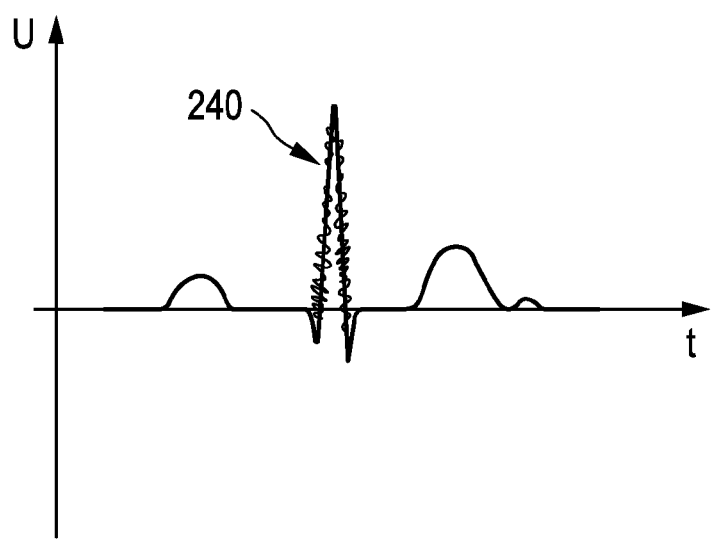
Figure 7C:
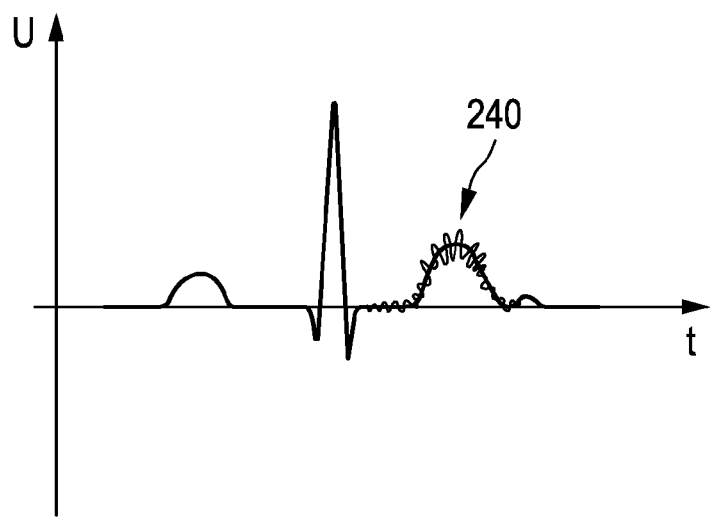

Therein, FIG. 7A shows the signal modulations 240 caused by the interference device 210 when it is at the position indicated in FIG. 6A, FIG. 7B shows the signal modulations 240 when the interference device 210 is at the position indicated in FIG. 6B, and FIG. 7C shows the signal modulations 240 caused by the interference device 210 when it is at the position indicated in FIG. 6C.

It has to be noted that the modulation 240 in FIG. 7 is only schematically shown. In practice, the whole ECG signal (not only the P wave of the ECG signal) will be modulated. Nevertheless, the strongest modulation 40 will in the above-mentioned example cure at the corresponding part of the ECG signal (in this example the P wave). During the measurement, the interference device 210 is moved through the heart 220 of the patient to a plurality of positions (examples are shown in FIGS. 6A, 6B and 6C) using the above-mentioned MPI technique. At the same time the position of the interference device 210 is tracked by the MPI apparatus 10, 30 and the ECG signal is recorded for every position of the interference device by the ECG device 151. As already mentioned above, these two pieces of information can then be brought into correlation with each other in the evaluation means, which is done as follows:

In a first step, the position of the highest modulation 240 is determined in the ECG signal. By measuring the time from the start of the ECG signal to the determined position where the highest modulation 240 occurs, one can determine the time the depolarization wavefront needs from the sinoarterial node to the place where the interference device 210 is positioned. In a next step, the position of the interference device 210 within the heart 220 of the patient 300 can be exactly determined using MPI imaging. Bringing the time-dependent information together with the information about a spatial position of the interference device thus means that it can be exactly determined how long the depolarization wave needs to propagate to a certainly known position. If this measurement procedure is repeated for many positions within the heart 220 of the patient 300, a very accurate image can be reconstructed showing the propagation of the depolarization wavefront of the patient's heart 220 over time.

Within this simulation of the propagation of the depolarization wavefront, many heart failures can be detected. For example, if the heart tissue is scarred in a specific region, this can be seen in the simulation since the depolarization wavefront will not pass this region, i.e. it will move around this region.

Figure 8A:
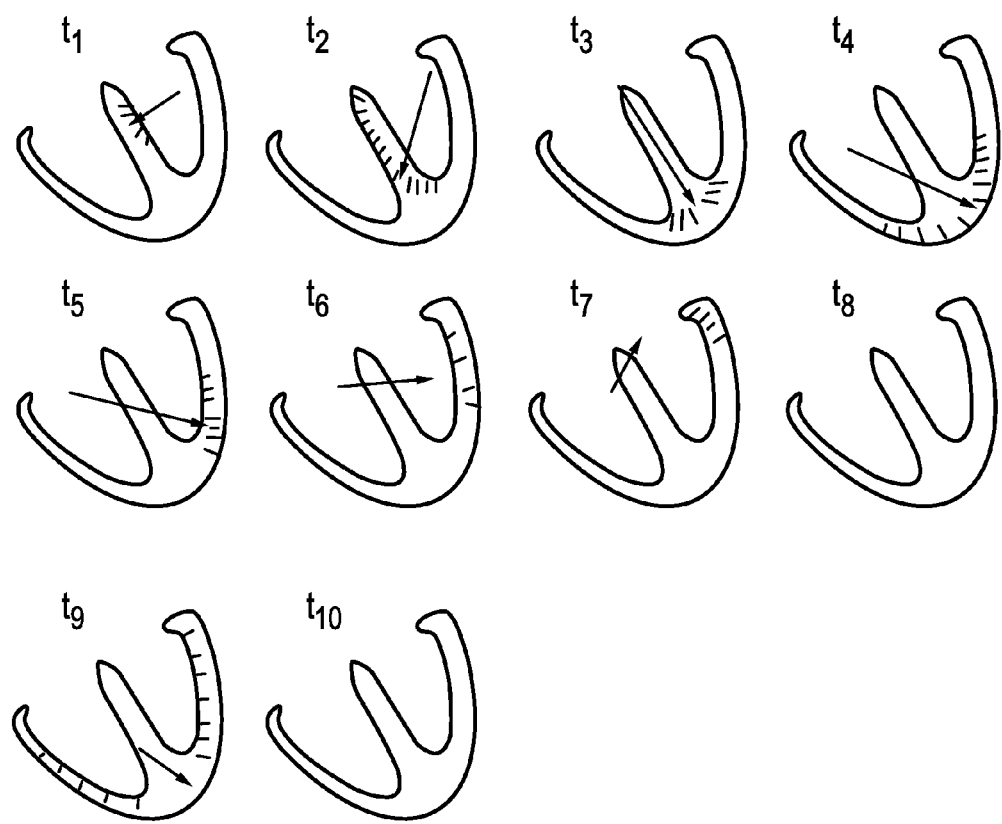
FIG. 8A shows a mean electrical vector of a depolarization wavefront of the heart over time.
Figure 8B:
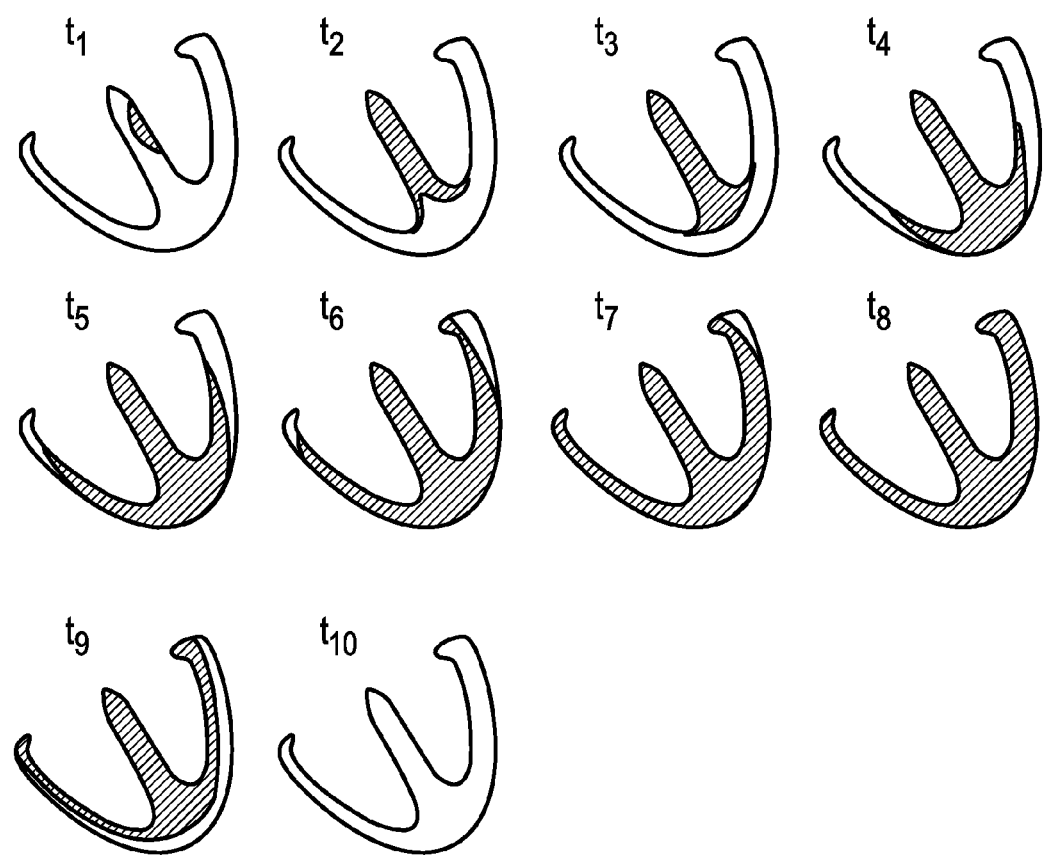
FIG. 8B shows the propagation of the depolarization wavefront of the heart over time.

The simulation of the propagation of the depolarization wavefront is exemplarily shown in FIG. 8B. The shaded regions therein represent electronegative regions which have been passed by the wavefront.

In practice, this simulation is usually done by the evaluation means (e.g. a computer). Similar to a regular vector ECG, a mean electrical vector is determined from the measurement values for every point in time. FIG. 8A exemplarily shows this mean electrical vector for the times $t_1$ to $t_{10}$. Therein, the mean electrical vector is schematically indicated by an arrow. The length of the arrow indicates the strength of the electrical field and the direction of the arrow indicates the sum of the electrical potential at the wavefront.

Summarizing, an apparatus and a method have been presented which allow a very accurate intracardiac electrocardiography by use of a magnetic and electrically conducting interference device. Since the measurements are taken intracardially, a very precise detection of heart failures can be accomplished. Even though the measurement is intracardially achieved, no serious surgical intervention is necessary compared to ECG mapping procedures using a catheter. Furthermore, the presented apparatus and method are advantageous since the interference device can be positioned in the patient's heart very accurately and at every desired position using the MPI technique. The apparatus and method according to the present invention therefore represent the true effort in modern heart diagnostic systems.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. An apparatus (100) for non-invasive intracardiac electrocardiography (ECG) by use of a magnetic and electrically conducting interference device (210), which apparatus comprises:
    ECG means (151, 230) for recording ECG signals,
    selection means comprising a selection field signal generator unit (110) and selection field elements (116), in particular selection field magnets or coils, for generating a magnetic selection field (50) having a pattern in space of its magnetic field strength such that a first sub-zone (52) having a low magnetic field strength and a second sub-zone (54) having a higher magnetic field strength are formed in a field of view (28),
    drive means comprising a drive field signal generator unit (130) and drive field coils (136a, 136b, 136c) for changing the position in space of the two sub-zones (52, 54) in the field of view (28) by means of a magnetic drive field so that the magnetization of the interference device (210) in the field of view (28) changes locally,
    receiving means comprising at least one signal receiving unit (140) and at least one receiving coil (148) for acquiring detection signals, which detection signals depend on the magnetization of the interference device (210) in the field of view (28), which magnetization is influenced by the change in the position in space of the first and second sub-zone (52, 54),
    control means (150) for controlling said signal generator units (110, 130) to generate and provide control currents to the respective field coils to generate appropriate magnetic fields for moving the interference device through the vessel system and the heart in a direction instructed by movement commands and/or for holding the interference device (210) at a constant position,
    processing means (154) for processing said detection signals acquired when appropriate magnetic fields are applied for determining the position of the interference device (210) within the vessel system and the heart from the processed detection signals, and
    evaluation means (153) for evaluating the influence of the interference device on the ECG signals recorded by the ECG means (151, 230).

2. An apparatus (100) as claimed in claim 1, wherein the ECG signals are recorded by the ECG means (151, 230) by use of skin electrodes which are arranged on the skin of the patient.

3. An apparatus (100) as claimed in claim 1, wherein the ECG signals are measured for a plurality of positions of the interference device (210).

4. An apparatus (100) as claimed in claim 1, wherein the evaluation means (153) are adapted for evaluating signal modulations of the ECG signals resulting from changes of the electrical field caused by the interference device (210).

5. An apparatus (100) as claimed in claim 4, wherein the evaluation means (153) are adapted for bringing the information about the signal modulations of the ECG signals caused by the interference device into correlation over time with the information about the position of the interference device (210) within the vessel system and the heart determined from the processed detection signals.

6. An apparatus (100) as claimed in claim 4, wherein the evaluation means (153) are adapted for determining the mean electrical vector of the depolarization wavefront of the heart over time at a spatially determined position by bringing the information about the signal modulations of the ECG signals caused by the interference device (210) into correlation over time with the information about the position of the interference device (210) within the vessel system and the heart determined from the processed detection signals.

7. An apparatus (100) as claimed in claim 4, further comprising quality improvement means for improving the evaluation of said signal modulations by comparing the measured signal modulations with expected signal modulations.

8. An apparatus (100) as claimed in claim 6, further comprising imaging means (153) for imaging the propagation of the depolarization wavefront over time.

9. An apparatus (100) as claimed in claim 1, further comprising focus means comprising a focus field signal generator unit (120) and focus field coils (126a, 126b, 126c) for changing the position in space of the field of view (28) by means of a magnetic focus field.

10. A method for non-invasive intracardiac electrocardiography (ECG) by use of a magnetic and electrically conducting interference device (210), which method comprises the steps of:
    recording ECG signals,
    generating a magnetic selection field (50) having a pattern in space of its magnetic field strength such that a first sub-zone (52) having a low magnetic field strength and a second sub-zone (54) having a higher magnetic field strength are formed in a field of view (28),
    changing the position in space of the two sub-zones (52, 54) in the field of view (28) by means of a magnetic drive field so that the magnetization of the interference device (210) in the field of view (28) changes locally,
    acquiring detection signals, which detection signals depend on the magnetization of the interference device (210) in the field of view (28), which magnetization is influenced by the change in the position in space of the first and second sub-zone (52, 54),
    controlling the generation of appropriate magnetic fields for moving the interference device through the vessel system and the heart in a direction instructed by movement commands and/or for holding the interference device (210) at a constant position, processing said detection signals acquired when appropriate magnetic fields are applied for determining the position of the interference device (210) within the vessel system and the heart from the processed detection signals, and evaluating the influence of the interference device (210) on the recorded ECG signals.

11. Computer program comprising program code means for causing a computer to control an apparatus as claimed in claim 1.

\* \* \* \* \*